United States Patent [19]
Badoz et al.

[11] Patent Number: 5,388,987
[45] Date of Patent: Feb. 14, 1995

[54] LASER BEAM DENTAL INSTRUMENT

[75] Inventors: Jean-Marie Badoz, Pontarlier/Doubs; Herve Picaud, Chatillon Le Duc; Jacques Manne, Besancon, all of France

[73] Assignee: Cheval Freres, SA, Miserey Salines, France

[21] Appl. No.: 776,320

[22] PCT Filed: Apr. 17, 1991

[86] PCT No.: PCT/FR91/00317
§ 371 Date: Dec. 16, 1991
§ 102(e) Date: Dec. 16, 1991

[87] PCT Pub. No.: WO91/16006
PCT Pub. Date: Oct. 31, 1991

[30] Foreign Application Priority Data

Apr. 17, 1990 [FR] France ................ 90 05037

[51] Int. Cl.⁶ .............................................. A61C 3/00
[52] U.S. Cl. ........................................ 433/29; 433/101; 606/18
[58] Field of Search .............. 433/29, 101, 215, 229; 606/2, 3, 10, 11, 13, 15, 16, 17, 18

[56] References Cited

U.S. PATENT DOCUMENTS

| | | | |
|---|---|---|---|
| 3,642,352 | 2/1972 | Beach | 606/18 |
| 4,316,467 | 2/1982 | Muckerheide | 128/303.1 |
| 4,336,809 | 6/1982 | Clark | 128/665 |
| 4,422,457 | 12/1983 | Hattori | 606/2 |
| 4,532,400 | 7/1985 | Toida et al. | 606/10 |
| 4,580,559 | 4/1986 | L'Esperance | 606/11 |
| 4,608,980 | 9/1986 | Aihara | 606/18 |
| 4,826,431 | 5/1989 | Fujimura et al. | 433/29 |
| 5,020,995 | 6/1991 | Levy | 433/215 |
| 5,207,576 | 5/1993 | Vassiliadis et al. | 606/18 |

FOREIGN PATENT DOCUMENTS

| | | |
|---|---|---|
| 0227258 | 7/1987 | European Pat. Off. . |
| 2598313 | 11/1987 | France . |
| 922311 | 3/1963 | United Kingdom . |
| 8906518 | 7/1989 | WIPO . |

*Primary Examiner*—John J. Wilson
*Attorney, Agent, or Firm*—Weiser & Associates

[57] ABSTRACT

Dental instrument for the treatment of caries and for oral surgery, of the type comprising a laser beam emission source, the said laser radiation being conveyed by optical fibre through the dental instrument (12) up to the zone to be treated, characterised in that it comprises control means enabling the user to vary at will during an operation at least one of the emission parameters of the laser beam chosen from the group comprising: the firing of the laser shot or shots, the energy of the laser beam, the frequency of the shots.

40 Claims, 3 Drawing Sheets

LASER BEAM DENTAL INSTRUMENT

BACKGROUND OF THE INVENTION

The subject of the present invention is a dental instrument for the treatment of caries and for oral surgery, of the type comprising a laser beam emission source, the said laser radiation being conveyed by optical fibre through the dental instrument up to the zone to be treated.

In what follows, a dental instrument employing laser radiation will be described specifically. It will be understood that this is in no sense limiting; the principles described will also be usable in surgery.

The sought-after aim is to obtain the painless ablation of hard or soft tissues (dentine, cement, pulp etc). For this purpose it is necessary to engender the vaporising, or even the sublimating, of these tissues without the tooth undergoing a rise in temperature and hence absorbing a significant quantity of energy or of power.

The lasers currently used in dentistry are provided with a light-conducting device which terminates in a hand-piece enabling use of the laser beam in the mouth. These hand-pieces are somewhat impractical to use since they are too bulky, this greatly hampering accessibility to the mouth, particularly when working at the back of the mouth. Moreover, these lasers are in general controlled by means of a programmed device which does not allow the practitioner, without interrupting the treatment, to adapt perfectly the laser operating parameters to the effects which he observes whilst operating. Finally, the purchase of a laser for a practitioner represents a high investment, which it is not currently possible to share out among several practices in the case of group practices, other than by moving all the laser equipment from one practice to the next.

SUMMARY OF THE INVENTION

The object of the invention is to remedy these disadvantages of the laser dental instruments of the prior art.

In accordance with the invention, this result is obtained with a dental instrument for the treatment of caries and for oral surgery, of the type comprising a laser beam emission source, the said laser radiation being conveyed by optical fibre through the dental instrument up to the zone to be treated, characterised in that it comprises control means enabling the user to vary at will during an operation at least one of the emission parameters of the laser beam chosen from the group comprising: the firing of the laser shot or shots, the energy of the laser beam, the frequency of the shots, and the optical fibre. According to a practical embodiment, the said control means are brought together, for example, in a pedal controlled by the user's foot and of the single, double or triple action type.

For optimal transmission of the laser beam, the dental instrument will comprise a stem and a head which are attached along secant axes in a rotatable manner to a connector into which opens the optical fibre conveying the laser beam from the source.

The parameters of the laser emission source must also be determined as a function of the following criteria:
painless operation
time of operating on caries from 30" to 1'30
good laser/tissue interaction
excellent general reliability of the equipment.

The basic laser parameters are preferably within the following ranges:
peak power:500 W to 10 KW
pulse length:10 $\mu$s to 200 $\mu$s
frequency of firing:0.5 Hz to 30 Hz.

It will be possible to obtain them on the basis of a laser with solid active medium excited or pumped by flash(es).

The active medium of the laser may be a doped crystal or a doped glass.

The table below indicates the nature of the material with its doping element or elements, together with the wavelength or range of wavelengths emitted:

| Active medium | Wavelengths in nm |
| --- | --- |
| Nd : YAG | 1064 |
| Cr : Nd : YAG | 1060 |
| Er : YAG | 2940 |
| Ho : YAG | 2060 |
| Cr : Nd : GSGG | 1060 |
| Cr : Nd : GGG | 1060 |
| Er : Nd : LiYF4 | 850-1047-1053 |
| Nd : YAP | 1060 |
| Alexandrite | 710-800 |
| Nd : phosphate glass | 1053.5 |
| Nd : silicate glass | 1053-1061 |

The use of a laser having these characteristics and in accordance with the present invention will be discussed more fully below. Such characteristics, in and of themselves, need not be described in greater detail since they will be readily understood by the person of ordinary skill in this art.

According to an important characteristic of the invention, the dental instrument can comprise, in addition to the laser beam source, at least one supplementary light source chosen from the following group and permitting one or more supplementary functions such as sterilisation and photopolymerisation of materials in the mouth:

a green light source centred on about 540 nm for sterilisation obtained by means of a dye-laser head;

an incoherent light source of about 540 nm consisting of a short-arc lamp and of a filter likewise used in sterilisation;

a blue light source for photopolymerisation, centred on 460 nm and obtained by means of the same short-arc lamp and a bandpass filter;

an incoherent light source use being made of both the bands centred on about 540 nm and about 460 nm, used in the two above functions.

The four sources will preferably be powered by means of the electronics of the above laser.

Finally, and according to an essential characteristic of the invention, the dental instrument will comprise a means permitting the same laser source to be connected to at least two different instruments and permitting the time-sharing use of these instruments by as many different users. The shared time will either be greater than the time of operating on a patient, or less than the firing period. It will permit multi-practice use of the laser and reduce the investment for each practice.

There will then be provided a means of communicating the use of the laser beam by the users.

This means also comprises safety of operation in multi-practice use.

Finally, with safety in mind, the dental instrument according to the invention will comprise a safety means so that there can be no laser emission in the rest position of the latter.

BRIEF DESCRIPTION OF THE DRAWINGS

The invention will be explained with the aid of the description below, made with reference to the attached drawings, given by way of non-limiting example, in which.

In all that follows, the elements appertaining to the laser proper and to its operation will not be described again. The data indicated earlier and the nature of the laser are sufficiently explicit for the person of ordinary skill in this art field.

DETAILED DESCRIPTION OF PREFERRED EMBODIMENTS

Figure 1:
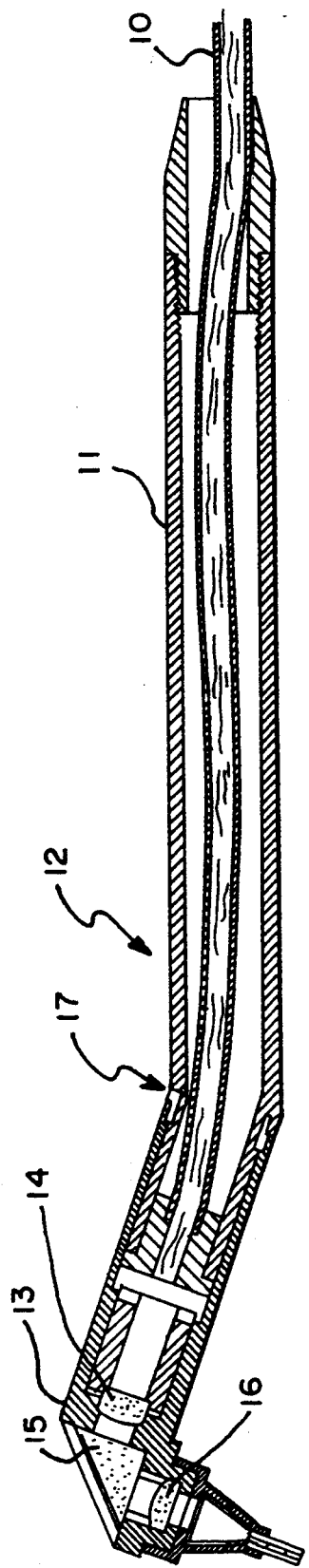
FIG. 1 is a horizontal sectional view of a handpiece specific to the use of a laser.
Figure 2:
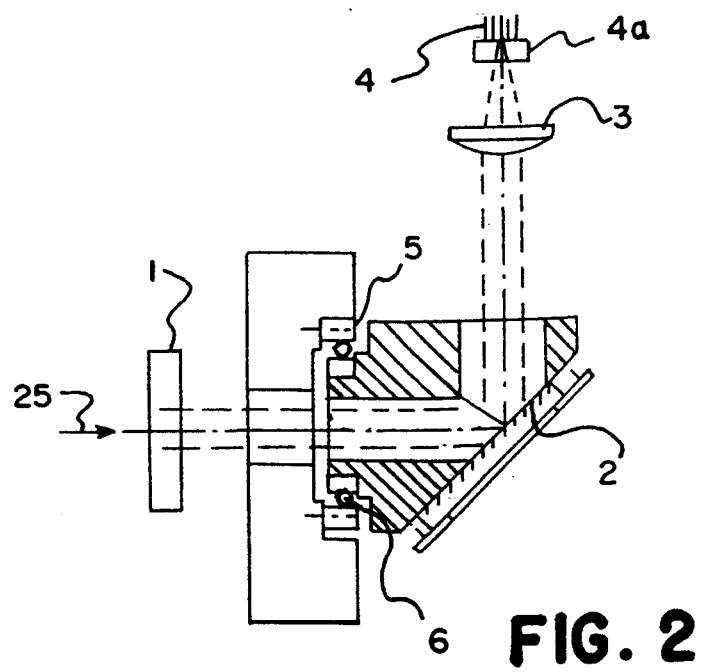
FIG. 2 is a diagrammatic sectional view of a system for reflecting the laser beam at 90° from the source.

Referring to FIGS. 1 and 2, and following the path of the laser beam 25 at its exit from the resonator via the coupling mirror (1), the beam is deflected at 90° by a laser reflecting mirror (2) (98% minimum mirror effect) which is transparent to the visible spectrum (40% minimum transmission). It is focused, via a lens or a convergent doublet (3), and given an anti-reflecting treatment for the wavelength of the laser, on the entrance face of the optical fibre (4). The fibre, equipped with a SMA-type connector, (4a) is made integral with an adjusting device endowed with three orthogonal translational degrees of freedom. The system permits the adjusting of the entrance face of the optical fibre and the positional locking, with levels of accuracy better than 0.02 mm, in the plane of the face of the fibre, and better than 0.1 mm on the longitudinal axis of the fibre.

The positional adjusting of the optical fibre is performed by an operator by means of an auxiliary and removable optical system.

In the case of the multi-fibre systems, the mirror (2) for 90° reflection towards the fibre is movable along a vertical axis. The advantage of moving along an axis contained by the plane of the mirror is that two types of default are allowed:

adjusting of the end-of-travel sensor so as to deliver a signal which appears before the mechanical end-of-travel;

the laser shot can be fired before the mirror is immobilised through a mechanical stop.

It will be possible for several mirrors of this type to be mounted in series, corresponding to a different optical fibre. Control and choice of the corresponding mirror and optical fibre is carried out by means of a pedal (schematically shown at 20 in FIG. 4).

This device is represented in FIG. 2 with a linear guiding on rails (5) with cylindrical rollers or balls (6).

The linear guiding should permit extreme accuracy of guiding the mirror, of the order of 1 to 2' of angle.

Figure 3:
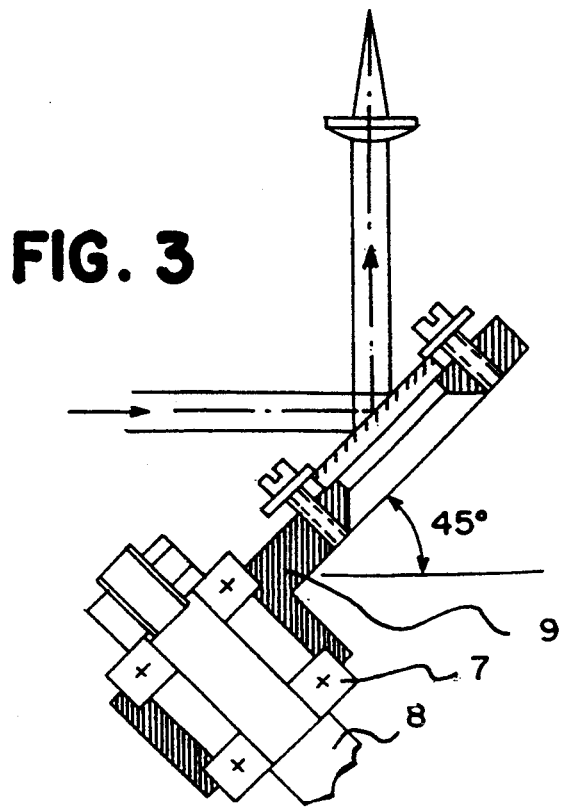
FIG. 3 is a variant of FIG. 2.

In the variant of FIG. 3, the guiding is performed by rotating on ball bearings (7) along an axis (8) perpendicular to the plane of the mirror, the mirror being supported by a rotatable stage (9).

Figure 4:
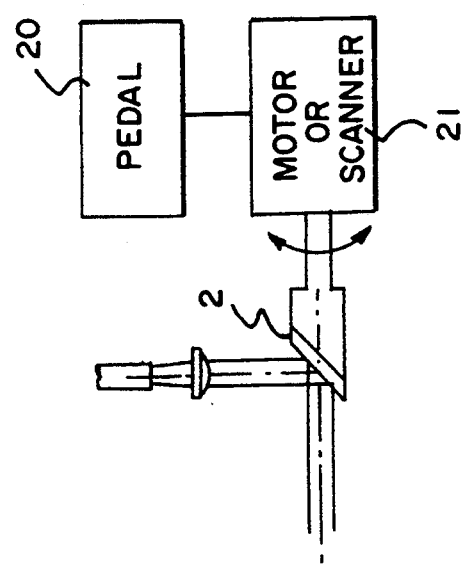
FIG. 4 is a variant embodiment for multi-practice
Figure 4A:
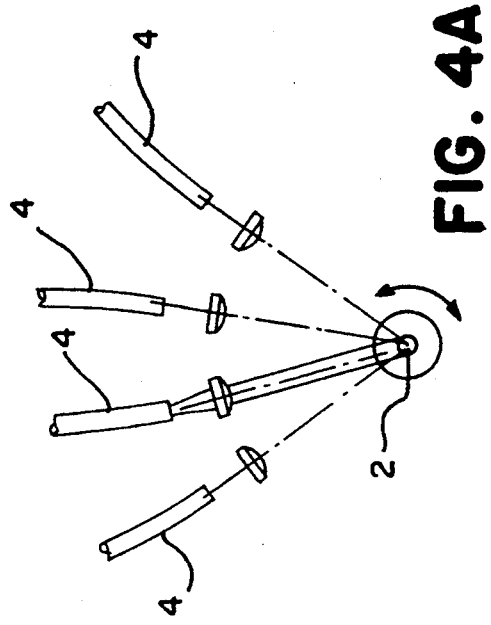
FIG. 4A is a top plan view of the variant which is shown in FIG. 4.

In the variant of FIG. 4, the mirror (2) is a mirror rotating by means of, for example, a stepped motor or a scanner (schematically shown at 21 in FIG. 4). It can thus point the laser beam towards any optical fibre (4) for multi-practice use.

Figure 5:
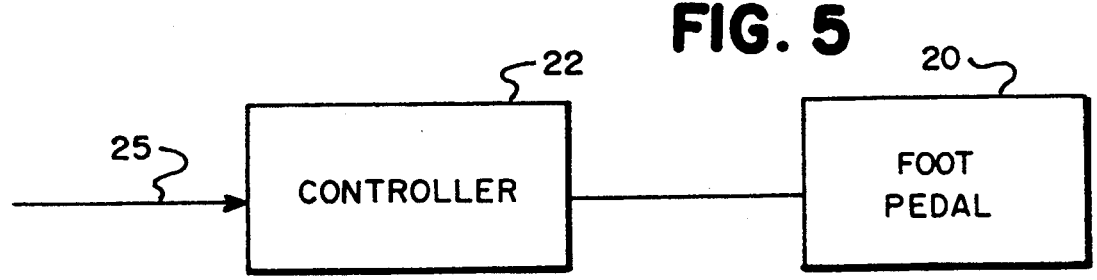
FIG. 5 is a block diagram of the laser controller.

Referring to FIG. 5, the laster beam (25 is controlled in the following manner by means of a controller (22) and the foot pedal (20).

It will be possible to use a single-action variable pedal. The angular movement of a slider or of the upper table about a vertical axis of the pedal acts on a potentiometer which controls the variation in energy.

As a variant, for a double-action variable pedal, there is furthermore provision for the angular movement about a horizontal axis acting on a second potentiometer which controls the variation in frequency.

In order to permit equally good utilisation in the seated and standing position, the pedal is preferably of robust construction and of modest height vertically in line with the operator's heel.

The optical fibre (4) is connected by the connector (4a) to an optical fibre (10) passing through the stem (11) of a hand-piece (12) represented in FIG. 1.

The head (13) of the hand-piece comprises:
an entrance lens (14),
a prism or plane mirror (15),
an exit lens (16).

The laser radiation is thus conveyed precisely at the head exit towards the zone to be treated.

Preferably, the head (13) will be rotatably mounted at (17) on the stem (11).

Internally, the stem and the head will comprise air passages for cooling.

The lens (16) may be changeable (and discardable), or possibly protected, by reason of the products of sublimation and of carbonization which may become deposited thereon.

Figure 6:
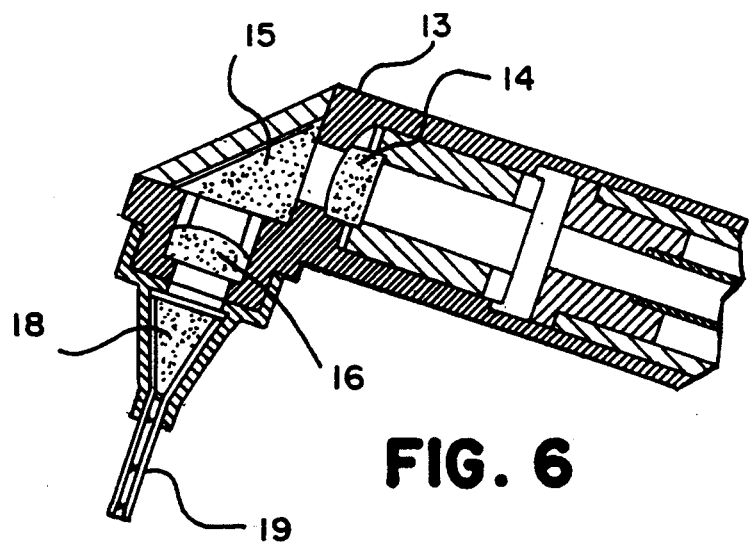
FIG. 6 is a partial, horizontal sectional view similar to FIG. 1, showing a variant of the exit head of the hand-piece.

In the variant of FIG. 6, the head exit will comprise an optical prism (18) with optical fibre (19) in particular in order to descend and operate in a dental canal.

There will also preferably be provision for the heads to be interchangeable so as to permit the following elements to be varied:
distances,
angles of attack,
focal lengths,
consumable contact optical fibre.

According to an advantageous variant embodiment, the instrument will comprise an aiming system injected into the optical fibre as visible light emitted by a laser diode of sufficient power to induce a supplementary anti-inflammatory analgesic effect intended to accelerate healing.

Figure 7:
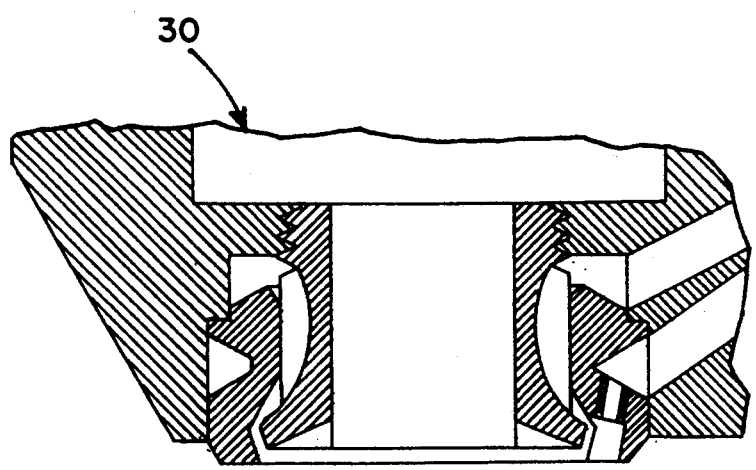
FIG. 7 is a partial sectional view of a variant of the exit head.

Furthermore, according to the variant of FIG. 7, it is possible to provide for the head to be equipped with a device (30) according to U.S. Pat. No. 5,078,601, assigned to MICRO MEGA, in order to limit the feedback of products of sublimation and of carbonization, this device being of the COANDA effect type.

We claim:

1. A dental instrument for treating caries and for oral surgery, comprising a laser beam emission source having a plurality of adjustable emission parameters including an adjustment for firing a laser beam in a shot or a series of shots, an adjustable energy level for the laser beam, and an adjustable frequency for firing of the laser beam, an optical fiber for conveying the laser beam extending through the dental instrument and to a zone to be treated, and control means responsive to a foot-controlled pedal, for varying each of the emission parameters of the laser beam during operation of the dental instrument.

2. The dental instrument of claim 1 wherein the foot-controlled pedal is a single action type.

3. The dental instrument of claim 2 wherein the foot-controlled pedal includes a sliding element coupled with a first potentiometer for variably controlling the energy level of the laser beam.

4. The dental instrument of claim 3 wherein the sliding element is further coupled with a second potentiometer for variably controlling the frequency of the firing of the laser.

5. The dental instrument of claim 1 wherein the foot-controlled pedal is a double action type.

6. The dental instrument of claim 1 wherein the foot-controlled pedal is a triple action type.

7. The dental instrument of claim 1 which further includes a supplementary source, in addition to the laser beam emission source, for providing a function supplementary to the treating of caries and the oral surgery.

8. The dental instrument of claim 7 wherein the supplementary function is sterilization, and wherein the supplementary source is a green light source centered on about 540 nm and obtained by means of a dye-laser head.

9. The dental instrument of claim 7 wherein the supplementary function is sterilization, and wherein the supplementary source is an incoherent light source of about 540 nm and obtained by means of a short-arc lamp associated with a filter.

10. The dental instrument of claim 7 wherein the supplementary function is photopolymerization, and wherein the supplementary source is a blue light source centered on about 460 nm and obtained by means of a short-arc lamp associated with a bandpass filter.

11. The dental instrument of claim 7 wherein the supplementary function is photopolymerization, and wherein the supplementary source is an incoherent light source emitted on bands centered on about 540 nm and about 460 nm, in combination.

12. The dental instrument of claim 7 wherein the supplementary function is an anti-inflammatory analgesic effect for accelerating healing, and wherein the supplementary source is injected visible light emitted by a laser diode.

13. The dental instrument of claim 1 which further includes means for connecting the laser beam emission source to a plurality of instruments.

14. The dental instrument of claim 13 which further includes means for distributing the laser beam emission source to the plurality of instruments on a time-sharing basis.

15. The dental instrument of claim 1 which further includes means for delivering the laser beam from the laser beam emission source to the dental instrument.

16. The dental instrument of claim 15 wherein the delivering means includes a coupling mirror at a resonator exit for the laser beam, a laser reflecting mirror in communication with the coupling mirror, for deflecting the laser beam by approximately 90 degrees, and means for focusing the deflected laser beam onto an entrance face of the optical fiber for delivering the laser beam to the dental instrument.

17. The dental instrument of claim 16 wherein the laser reflecting mirror has a 98 percent minimum mirror effect and is substantially transparent to light in the visible spectrum.

18. The dental instrument of claim 17 wherein the laser reflecting mirror has a minimum transmission of 40%.

19. The dental instrument of claim 16 wherein the focusing means is a lens.

20. The dental instrument of claim 16 wherein the focusing means is a convergent doublet.

21. The dental instrument of claim 16 wherein the focusing means has a face which is provided with an anti-reflecting treatment for wavelengths of the laser beam.

22. The dental instrument of claim 16 wherein the entrance face of the optical fiber is provided with a connector of the SMA type.

23. The dental instrument of claim 16 wherein the optical fiber is integral with means for adjusting the optical fiber along three orthogonal translational degrees of freedom.

24. The dental instrument of claim 23 wherein the integral adjusting means includes means for adjusting the position of the entrance face of the optical fiber and means for positional locking of the optical fiber.

25. The dental instrument of claim 24 wherein the integral adjusting means has an accuracy of at least 0.02 mm along a plane defined by the entrance face of the optical fiber, and at least 0.1 mm along a longitudinal axis defined by the optical fiber.

26. The dental instrument of claim 16 wherein the laser reflecting mirror is movable, for communicating with a plurality of optical fibers.

27. The dental instrument of claim 26 wherein the laser reflecting mirror includes linear guide rails in association with cylindrical bearing means, for movement of the laser reflecting mirror.

28. The dental instrument of claim 26 wherein the laser reflecting mirror includes ball bearings positioned along an axis perpendicular to a plane defined by the laser reflecting mirror, for supporting the laser reflecting mirror upon a rotatable stage.

29. The dental instrument of claim 26 which further includes means for rotating the laser reflecting mirror.

30. The dental instrument of claim 29 wherein the rotating means is a stepped motor.

31. The dental instrument of claim 29 wherein the rotating means is a scanner.

32. The dental instrument of claim 29 which further includes a foot-controlled pedal having means for controlling the rotating means.

33. The dental instrument of claim 1 wherein the dental instrument is a hand-piece having a head which includes an entrance lens in communication with the optical fiber, means for reflecting the laser beam received from the optical fiber at a specified angle, and an exit lens for delivering the reflected laser beam from the head.

34. The dental instrument of claim 33 wherein the reflecting means is a plane mirror.

35. The dental instrument of claim 33 wherein the reflecting means is a prism.

36. The dental instrument of claim 33 wherein the head is rotatably mounted to a stem of the hand-piece, 37. The dental instrument of claim 33 wherein the exit lens is changeably mounted within the head.

38. The dental instrument of claim 33 wherein the exit lens includes means for protection against products of sublimation and carbonization.

39. The dental instrument of claim 33 wherein the head further includes an exit portion which includes means for developing a COANDA effect.

40. The dental instrument of claim 33 wherein the head further includes an exit portion which incorporates an optical prism in combination with an optical fiber for operating within a dental canal.

* * * * *